(12) United States Patent
Turrini et al.

(10) Patent No.: US 10,596,022 B2
(45) Date of Patent: Mar. 24, 2020

(54) BIAXIAL MULTICENTRE ARTICULATED COUPLING FOR ORTHOPEDIC ORTHOSES OR BRACES DESIGNED FOR JOINT REHABILITATION

(71) Applicant: F.G.P. S.R.L., Dossobuono (IT)

(72) Inventors: Alberto Turrini, Dossobuono (IT); Moreno Ferrigolo, Dossobuono (IT)

(73) Assignee: F.G.P. S.R.L., Dossobuono (IT)

( * ) Notice: Subject to any disclaimer, the term of this patent is extended or adjusted under 35 U.S.C. 154(b) by 398 days.

(21) Appl. No.: 15/550,639

(22) PCT Filed: Jan. 15, 2016

(86) PCT No.: PCT/EP2016/050778
§ 371 (c)(1),
(2) Date: Aug. 11, 2017

(87) PCT Pub. No.: WO2016/131571
PCT Pub. Date: Aug. 25, 2016

(65) Prior Publication Data
US 2018/0036159 A1    Feb. 8, 2018

(30) Foreign Application Priority Data

Feb. 18, 2015 (IT) .............................. BO2015A0079

(51) Int. Cl.
*A61F 5/01* (2006.01)

(52) U.S. Cl.
CPC ............ *A61F 5/0102* (2013.01); *A61F 5/013* (2013.01); *A61F 5/0123* (2013.01);
(Continued)

(58) Field of Classification Search
CPC ...... A61F 5/0102; A61F 5/013; A61F 5/0123; A61F 2005/0132; A61F 2005/0139;
(Continued)

(56) References Cited

U.S. PATENT DOCUMENTS

| 4,599,998 A | 7/1986 | Castillo |
| 6,527,733 B1 | 3/2003 | Ceriani et al. |

(Continued)

OTHER PUBLICATIONS

International Search Report for PCT/EP2016/050778, 3 pages.
written Opinion of the International Searching Authority for PCT/EP2016/050778, 5 pages.

*Primary Examiner* — Tarla R Patel
(74) *Attorney, Agent, or Firm* — Ference & Associates LLC

(57) ABSTRACT

An articulated coupling or joint (10) for orthopedic braces or orthoses comprises a pair of bars or uprights (14, 15), a proximal end of each of these being rotatingly mounted around an axis defined by its rotation pin (25), this proximal end of the bars or uprights being toothed and engaging with a common grooved cylindrical cursor (20) translatable along an additional axis, the other distal end of the respective bars (14, 15) being fixable to a portion of the body of the patient to be treated. Each bar or upright (14, 15) is mounted on a respective element (12, 13) on which the respective rotation pin (25) is mounted and which itself is rotatingly mounted on an additional pin (18) coaxial with the additional axis; moreover, the additional pin (18) is mounted on a platform (11), a surface of which rests against the body of a patient to be treated, the two bars (14, 15) thus being able to simultaneously rotate both around their own primary centres of rotation represented by their rotation pins (25) and around a common centre of rotation represented by the additional pin (18).

4 Claims, 3 Drawing Sheets

(52) U.S. Cl.
CPC ............... *A61F 2005/0132* (2013.01); *A61F 2005/0134* (2013.01); *A61F 2005/0137* (2013.01); *A61F 2005/0139* (2013.01)

(58) Field of Classification Search
CPC ...... A61F 2005/0137; A61F 2005/0134; A61F 5/0106; A61F 5/0118
See application file for complete search history.

(56) References Cited

U.S. PATENT DOCUMENTS

| | | | |
|---|---|---|---|
| 10,098,774 B2* | 10/2018 | Modglin | A61F 5/01 |
| 2009/0118656 A1* | 5/2009 | Ingimundarson | A61F 5/0123 602/26 |

* cited by examiner

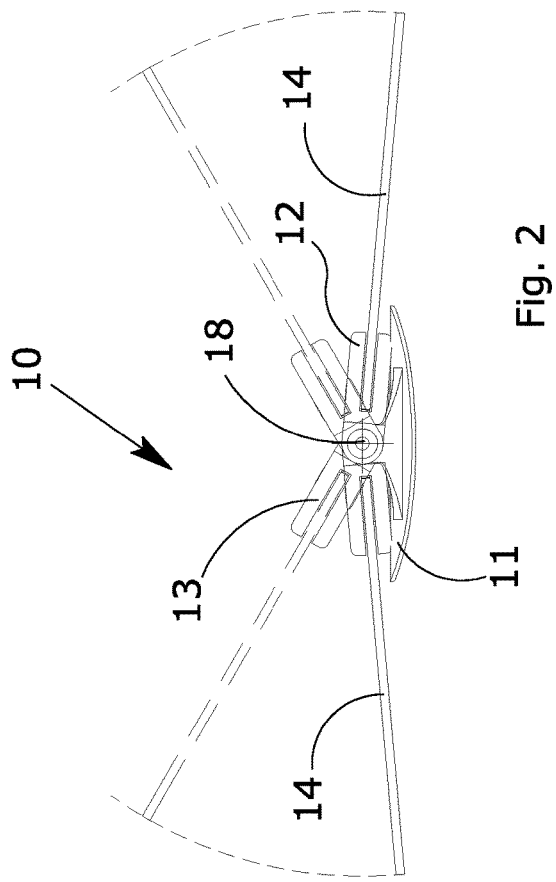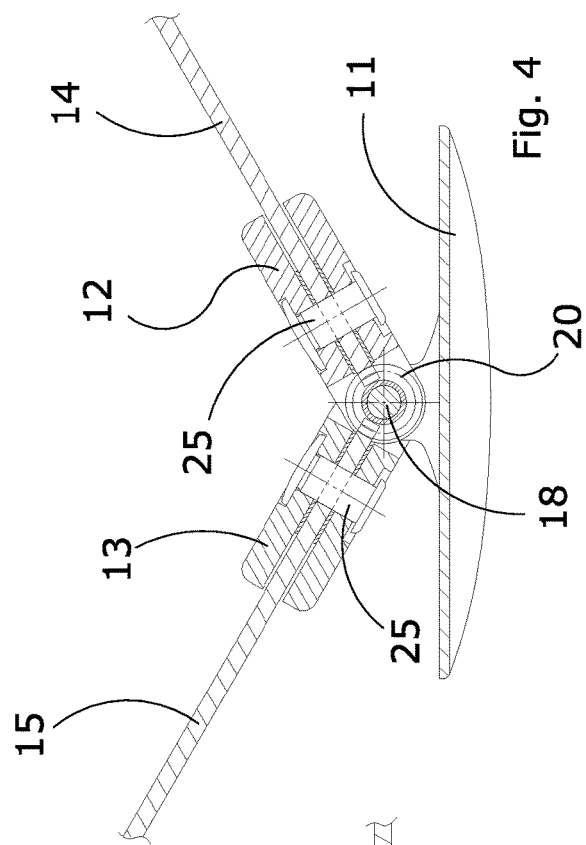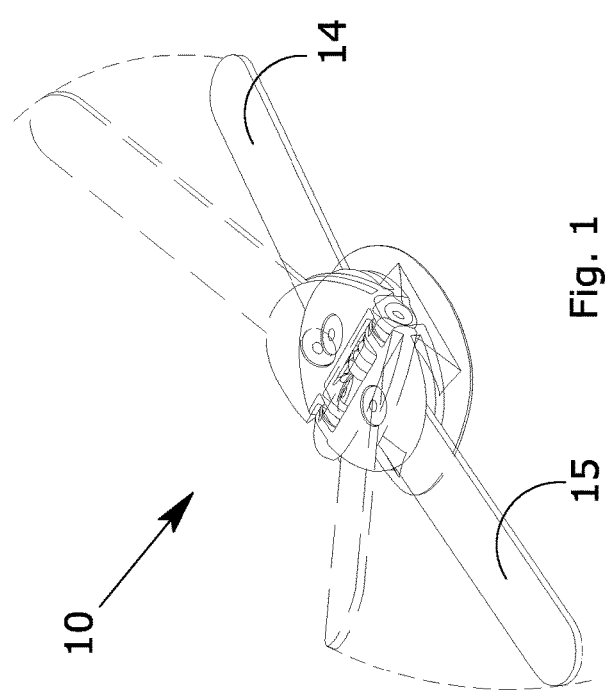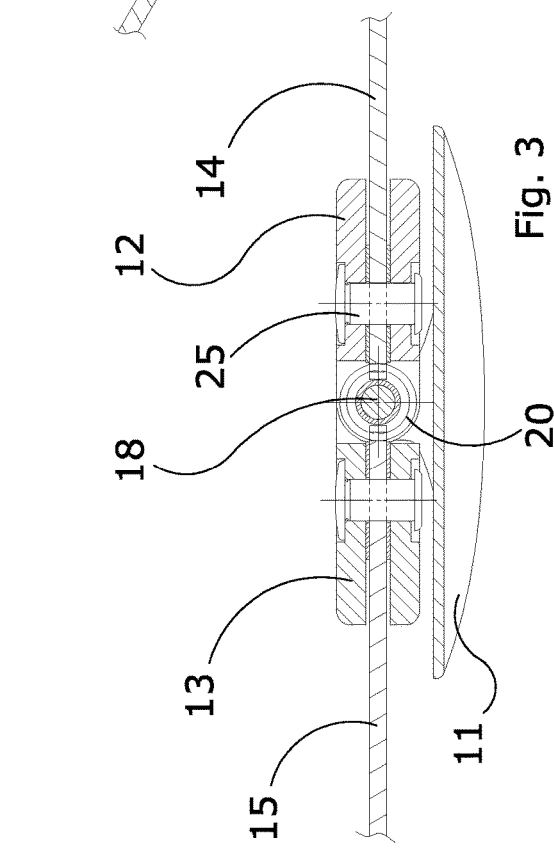

BIAXIAL MULTICENTRE ARTICULATED COUPLING FOR ORTHOPEDIC ORTHOSES OR BRACES DESIGNED FOR JOINT REHABILITATION

TECHNICAL FIELD

This invention concerns a biaxial multicentre articulated coupling for orthopedic orthoses or braces designed for rehabilitation of joints of the human body, such as the knee, the elbow, the ankle, the shoulder or similar.

This solution foresees the production of a brace with features designed to correct certain problems of the joints of the knee, the elbow or of other joints, mainly connected to the problem of varus or valgus deformity.

It should be remembered that, at present, the two bars that make up a traditional multicentre articulation are connected together thanks to a circular toothed profile present on each bar and that this toothed profile places them in relative and synchronous motion with respect to each other and that, by definition, the rotation centres enable the bars to rotate only on one plane around two parallel axes, making it possible to create transverse thrusts only by means of special filling elements.

On the contrary, the articulated coupling according to the invention foresees that the two primary centres of the bars are in turn fixed on a single-centre system that thus removes the restraint of parallelism of the axes, with the possibility of creating transverse thrusts with respect to the angular movement plane of the joint, creating a structure that can be used to correct axial deviations of the joints.

This invention can be applied in the medical and orthopedic industry and in particular in the production of braces in general, as well as of prostheses and orthoses mainly used in conservative, post-traumatic, re-educational and post-operative therapy.

BACKGROUND ART

It is known that subjects presenting orthopedic problems involving the knee joint, but similarly also of other joints, such as the ankle or the elbow, above all in the case of injuries or as a result of a previous surgical operation, require the use of an orthopedic brace, or orthosis, designed to guarantee or control the hinge restraint function between the femur and the tibia or other articulated joint points, supporting stress which would otherwise be harmful for the joint.

The function of an orthosis is, in general, that of guaranteeing the relative immobilization or limitation of a joint affected by trauma, by arthrosis, by sprained ligaments or which has undergone a surgical operation.

Another use of orthoses is for the concomitant functional rehabilitation or re-education, wherein the orthosis can be used to reduce the load on the joint and reduce the pain, or can be used for prevention in cases of osteoporosis or bone weakness.

An orthosis usually comprises a rigid or soft frame, encircling the limb, designed to guarantee adequate harnessing of the joint in order to prevent the onset of stress on the ligaments or on the synovial membranes during walking by the injured and/or convalescent subject.

According to background art, the frame of an orthosis for joints, for example in the typical case of a knee brace, comprises means of restraint to the femur and the tibia and a section of connection of these means consisting of an articulated coupling positioned at the level of the knee.

The means of restraint usually consist of preformed bars that are fixed by means of suitable straps encircling both the femur and the tibia of the injured subject or fabric bands, straps or sleeves that make it possible to create a restraint between the ends of the mechanical articulated coupling and the limb.

The mechanical articulated coupling is positioned laterally with respect to the femur and the tibia, in the case of application, for example, to the leg. Thanks to its conformation consisting of 2 rotation centres relatively restrained to each other by toothed profiles, this articulated coupling follows the kinematic of the knee with good approximation.

A standard multicentre articulated coupling is a system consisting of two hinged bars, each one hinged to its own centre of rotation, wherein these centres of rotation are restrained parallel to each other and at a known distance.

In the standard multicentre articulated coupling, the two bars are connected to each other thanks to a circular toothed profile present on each bar, and this toothed profile places them in relative and synchronous motion with respect to each other.

In this articulated coupling, by definition, the rotation centres and the toothed profile, enable the bars to rotate only around two parallel axes and their rotation motion thus lies on one plane.

Among the problems that can affect a joint are varus and valgus deformities, which constitute skeletal abnormalities causing axial deviations of the limb, wherein the skeletal segments, situated distally with respect to the section in which the deviation occurs, are in the abnormal position of abduction in valgus deformities and adduction in varus deformities, that is to say in the first case farther away and in the second case closer with respect to the mid-line of the body.

The most typical case concerns the knees which, if suffering from a varus deformity, tend to be spread apart towards the outside of the body with respect to the undeformed axis of the limb. Vice versa, in cases of valgus deformities, the knees tend to point inwards and be closer to each other.

In both of the cases of deformity described above, the subject tends to experience greater difficulty in walking the narrower the open obtuse angle is inwards in the case of a varus deformity or outwards in the case of a valgus deformity.

There are various known solutions to this problem, for example through the use of special knee braces or orthoses aimed at correcting the misalignment of the joint, generally through the use of shims of various types inserted inside the brace close to the lateral thrust area to be fitted on the articulated coupling.

More in general, traditional background art orthopedic braces are, by definition, made using rotation centres that enable the bars to rotate only on one plane around two parallel axes, preventing the creation of lateral thrusts to correct problems such as those relative to varus and valgus deformities, which are achieved by using special filling elements such as spacers or shims of various kinds.

While clinically and at least partially resolving limb deformities, the solutions proposed so far are not without drawbacks substantially connected with the use of the orthosis.

One problem is represented by the fact that these braces are difficult to adjust, especially when in use; in fact, a gradual recovery of the limb requires continuous measurement of the obtuse angle between femur and tibia, in the case of the knee, with consequent adaptation of the orthosis, particularly as regards its rigid frame.

Another drawback is represented by the fact that these braces are sometimes difficult to wear as they consist of several reciprocally connected portions that can be fixed by any appropriate means of temporary blocking.

The document U.S. Pat. No. 4,599,998 describes an articulated coupling for orthopedic braces comprising a pair of bars rotating around respective fixed pins mounted on a platform. The ends of these bars are toothed and engage with a toothed cursor mounted on a support fixed to the platform and translatable along an axis parallel to the plane of the platform.

DESCRIPTION OF THE INVENTION

The aim of this invention is to provide an innovative multicentre articulated coupling for orthopedic braces or orthoses designed for the rehabilitation of the knee or other orthopedic braces that can be fitted as aids for the joints of the human body, such as the ankle, the elbow or similar, which is able eliminate or at least reduce the above-mentioned drawbacks.

The invention also proposes to provide an articulated coupling for orthopedic braces or orthoses designed for joint rehabilitation which is made in such a way as to allow the possibility of eliminating the restraint of parallelism of the axes, thus being adaptable to resolve the problems relative to varus and valgus deformities of the joints to be treated or also in cases wherein the joint develops a natural varus or valgus angle as in the case of the elbow.

This is achieved by means of an articulated coupling for orthopedic braces or orthoses designed for limb rehabilitation, whose features are described in the main claim.

The dependent claims of the solution according to this invention describe advantageous embodiments of the invention.

The main advantages of this solution concern first of all the fact that, with respect to known solutions, the articulated coupling presents a biaxial multicentre type construction, with the two (primary) rotation centres of the bars fixed in turn on a single-centre system that thus eliminates the restraint of parallelism between the axes.

By introducing this new (secondary) rotation centre, the bars are able to rotate around the primary centre of rotation and around this new common centre.

A circular grooved cursor, which slides along the axis of the secondary rotation centre, allows the bars to remain connected to each other even when they rotate around the secondary rotation centre, becoming in fact detached from the original rotation centre.

DESCRIPTION OF THE DRAWINGS

Other features and advantages of the invention will become clear on reading the description given below of one embodiment, provided as a non-limiting example, with the help of the accompanying drawings, in which:

FIGS. 1 to 4 show schematic views of the articulated coupling according to the invention, equipped with a single-centre system that eliminates the restraint of parallelism between the axes, the bars also being able to rotate around this new common centre;

DESCRIPTION OF AN EMBODIMENT OF THE INVENTION

Figure 6:
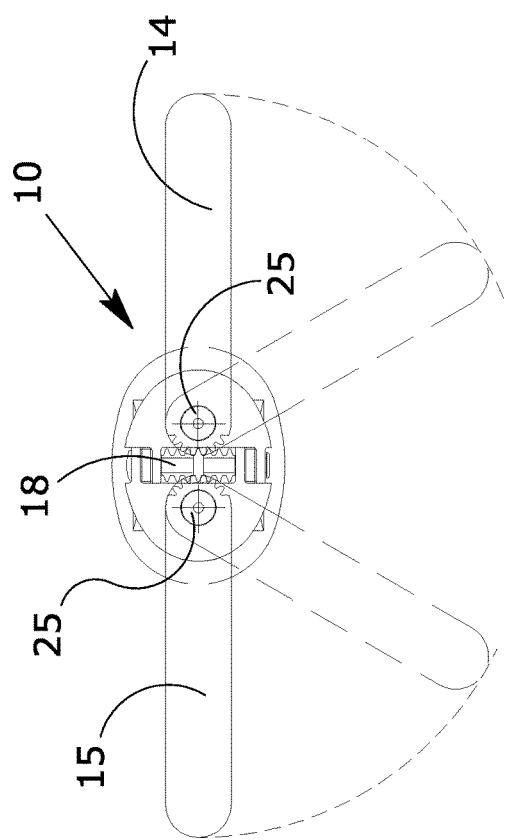
FIGS. 5 to 8 are schematic views showing the possibility of rotation of the bars around their primary centre of rotation.
Figure 8:
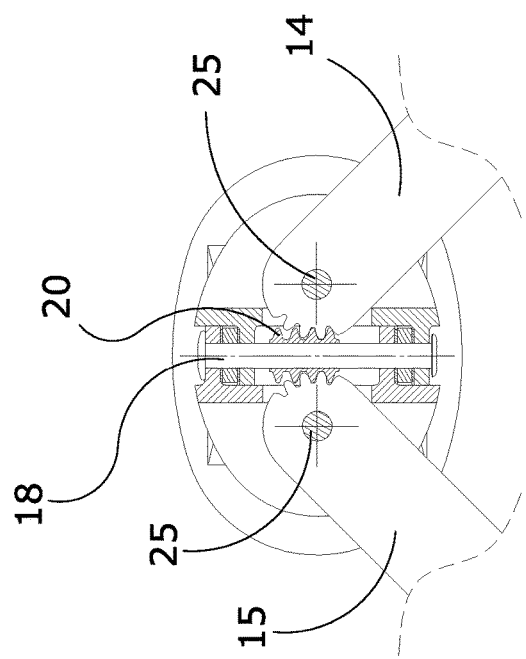
Figure 5:
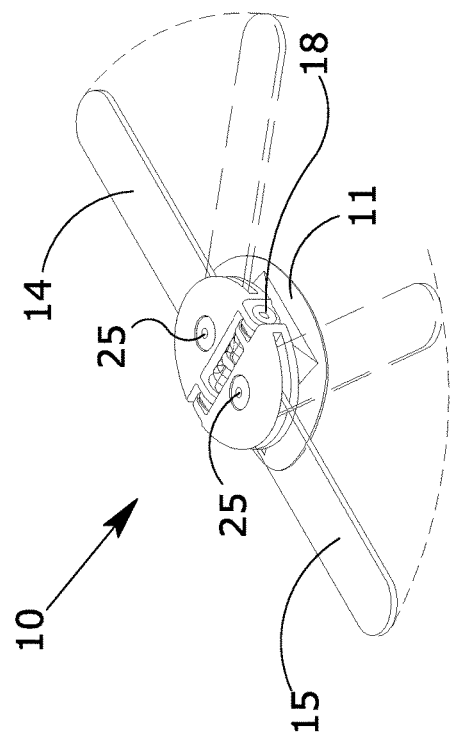
Figure 7:
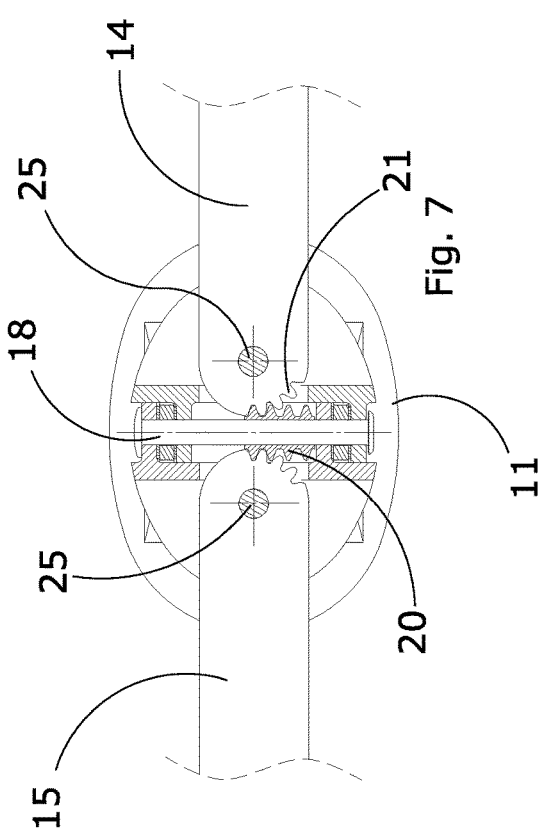
Figure 9:
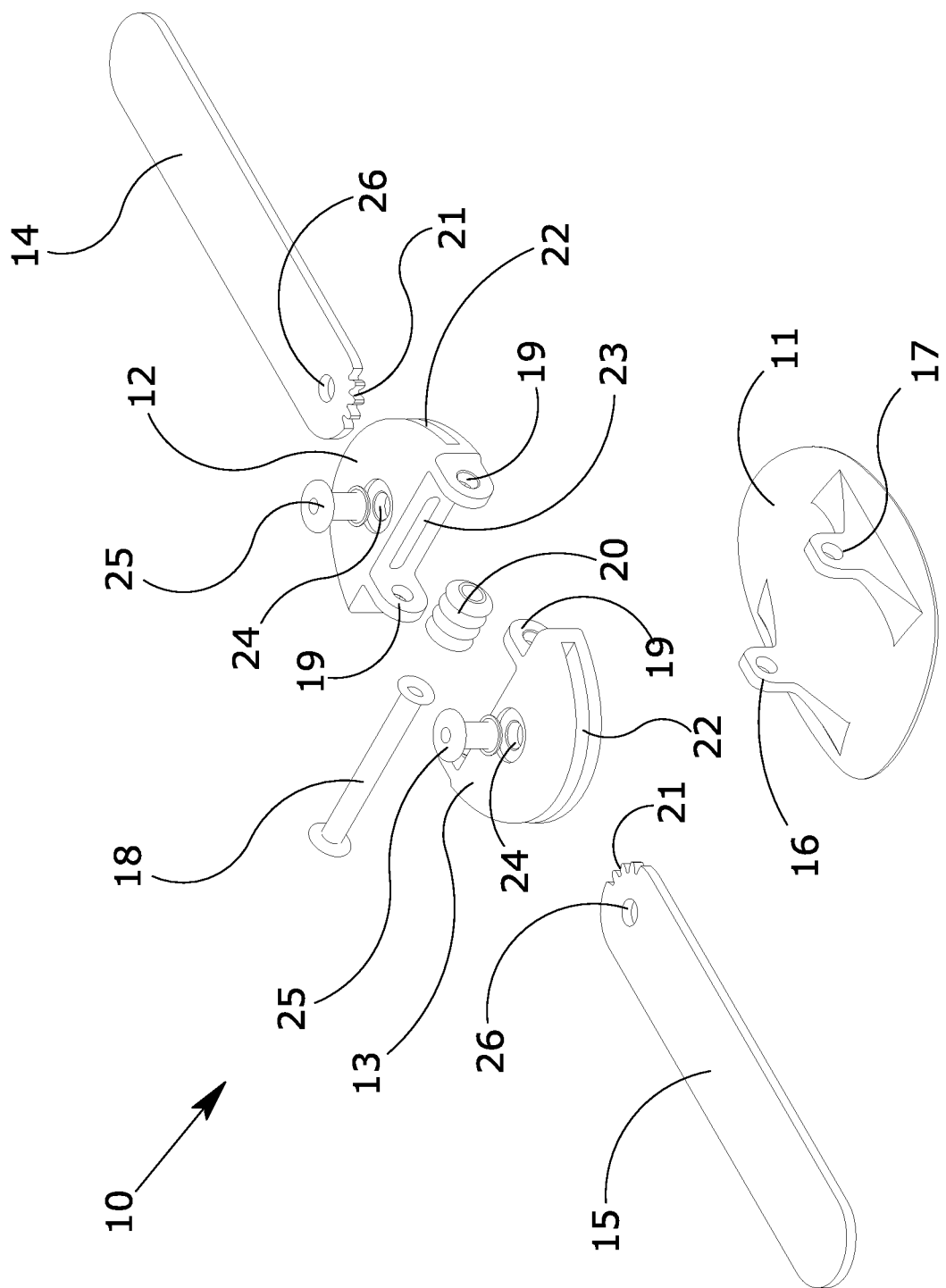
FIG. 9 is a prospective schematic exploded view of the articulated coupling according to the invention.

With reference to FIG. 9, the numeral 10 denotes in its entirety a biaxial multicentre articulated coupling, for human joints, according to the invention.

The articulated coupling 10 according to the invention comprises a platform 11 which rests against the part of the body to be treated, such as for example the knee, the elbow, or other parts, and on which two elements 12 and 13 are rotatingly mounted and which accommodate in rotation the proximal longitudinal ends of respective bars or uprights 14 and 15 which can be fixed by their respective distal ends to the part of the body to be treated, such as to the femur and the tibia in the case of the leg, or to the humerus and the ulna in the case of the arm, or to other parts of the body close to the joint to be treated.

More specifically, the platform 11 comprises two protrusions 16 and 17 each provided with a hole designed to accommodate a pin 18 on which the two elements 12 and are hinged by means of the perforated forks 19 with which they are provided.

In addition, an axially perforated cylindrical cursor 20 is slidingly mounted on the pin 18 and is provided with circular grooves that engage with respective toothed edges 21 of the bars 14 and 15.

Each of the two elements 12 and 13 is substantially semi-circular and presents a groove 22 cut in the entire circle arc and in the centre-line of the middle plane, the groove terminating at the inner wall of the respective half-body at an opening 23 which opens on to the centre of the coupling close to the cursor 20 of the pin 18.

In addition, each of the two elements 12 and 13 has a transverse hole 24 cut in the semi-circular surface, designed to accommodate a respective rotational pin 25 that also intercepts a hole 26 cut in the bars 14 and 15. Each respective rotational pin 25 thus represents the axis around which a bar 14, 15 rotates on a plane parallel to the semicircular surface of each element 12, 13.

The assembly of the articulated coupling thus foresees the insertion of the two elements 12 and 13 and of the cylindrical cursor 20 with circular grooves on the platform 11, keeping the holes of the forks 19 and of the cursor 20 aligned with those of the protrusions 16 and 17 of the platform 11, and thus the insertion of the pin 18 which acts as a rotation axis for the two elements 12 and 13.

At the same time, the bars 14 and 15 are inserted in the grooves 22 in the two elements 12, 13, positioning the toothed profiles to protrude from the openings 23 onto the grooved surface of the cursor 20. The pins 25 are then inserted in the holes 24 of the elements 12, 13, and in the holes 26 of the bars 14 and 15.

When in use, it is possible to obtain two (primary) centres of rotation on the respective planes parallel to the semicircular surfaces of the elements 12, 13 by the pins 25 of the bars 14 and 15 which rotate as shown in FIGS. 5 to 8, and a (secondary) single-centre system defined by the pin 18 which eliminates the restraint of parallelism of the axes of the bars which can move angularly in "wing-beat" style as shown in FIGS. 1 to 4, rotating simultaneously around the axis defined by the pin 18, which lies on a plane parallel to the surface of the platform 11.

Each bar 14 and 15 is therefore able to rotate both around its own primary centre of rotation represented by the rotational pin 25 and around a common centre of rotation represented by the additional pin 18.

The circular grooved cursor 20, which slides along the pin 18 that defines the axis of the secondary centre of rotation, allows the bars to remain connected to each other even when they rotate around the secondary centre of rotation, detaching themselves, in effect, from the original centre of rotation.

From an operational point of view, the introduction of the secondary centre of rotation, which frees the bars from merely rotating on their own plane, makes it possible to also apply lateral thrusts on the joint which are useful in axial correction, such as in valgus and varus deformities or when it is necessary to carefully monitor joints which by nature develop a varus or valgus angle, such as for example the elbow.

The articulated coupling 10 according to the invention can be made from lightweight metal alloy or high-resistance composite plastic material.

The invention as described above refers to a preferred embodiment. It is nevertheless clear that the invention is susceptible to numerous variations falling within the scope of the disclosure, in the context of technical equivalents, such as for example the introduction of solutions that restrain the angle of rotation on both the primary axis and the secondary axis, in order to limit what is known in orthopedics as ROM (Range of Movement) for a joint that needs a brace or orthosis.

The invention claimed is:

1. An articulated coupling or joint for use on an orthopedic brace or orthosis comprising two bars or uprights, a proximal end of each bar or upright being rotatable around an axis defined by a respective rotation pin, each proximal end of these bars or uprights being toothed and engaging with a grooved cylindrical cursor translatable along an additional axis, whereby a distal end of each respective bar or upright is intended to be fastened to a portion of a patient's body, wherein each bar or upright is associated to a respective element on which the respective rotation pin is mounted, the respective element being rotatable around an additional pin that is placed in plane with said additional axis, said additional pin being mounted and in the same plane on a platform, whereby the two bars or uprights are able to simultaneously rotate both around their own primary rotation centers represented by their respective rotation pins, as well as around a rotation center represented by said additional pin, wherein the platform comprises two protrusions, each protrusion being provided with a hole designed to house the additional pin on which each respective element is hinged on a respective perforated fork.

2. The articulated coupling or joint of claim 1, wherein the grooved cylindrical cursor has an axial through hole and is slidingly mounted on said additional pin, whereby it further comprises a plurality of circular grooves which engage with respective toothed ends of said bars or uprights.

3. The articulated coupling or joint of claim 1, wherein each respective element is substantially semi-circular and has a groove cut in an entire circle arc and in a centerline of a middle plane, the groove terminating at the inner wall of the respective element at an opening which opens on to the center of the coupling or joint close to the cursor of the additional pin.

4. The articulated coupling or joint of claim 1, each respective element having a transverse hole cut in a semi-circular surface, said transverse hole accommodating a respective rotation pin that intercepts a hole cut in each respective bar or upright.

* * * * *